Figure 1:
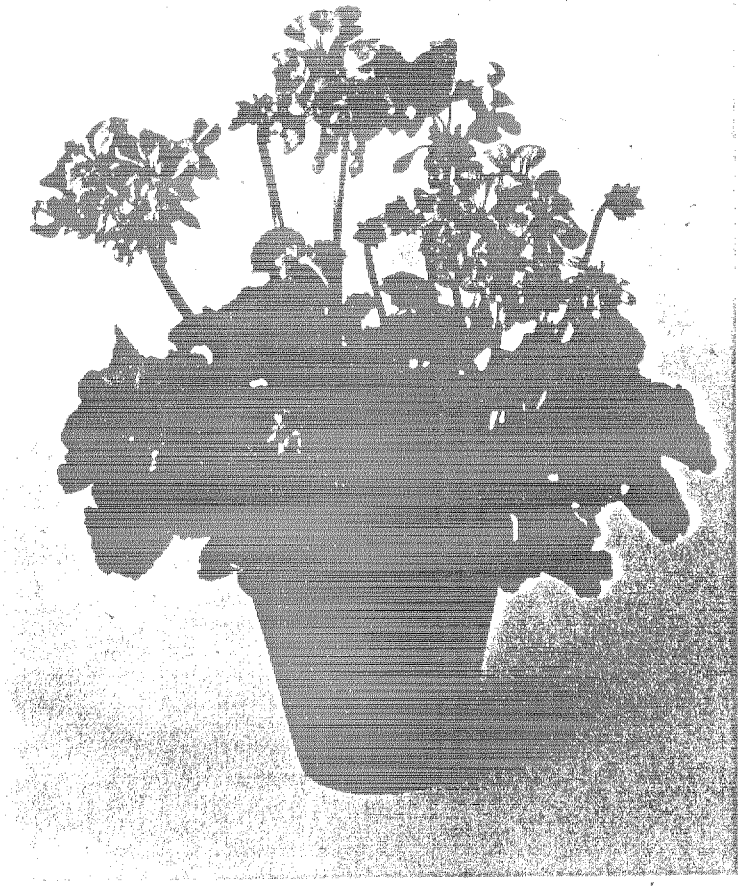
Figure 2:
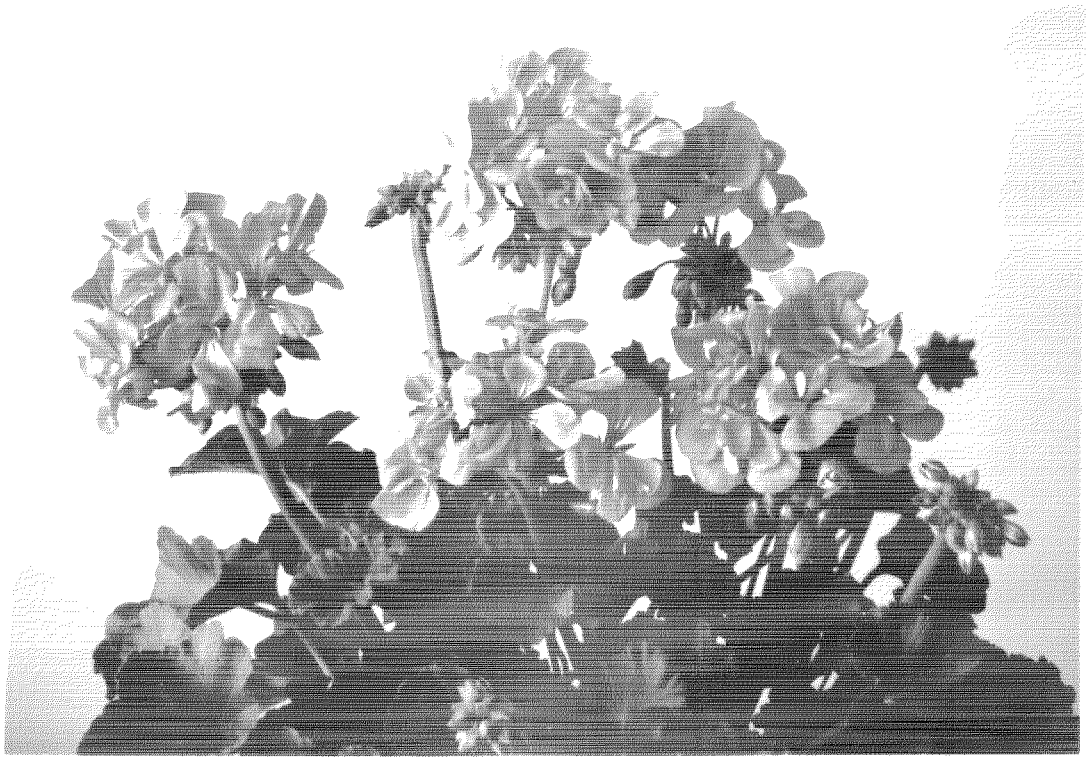

PLT-325 SR
C5203 OR PP 005,369

FIG. 3
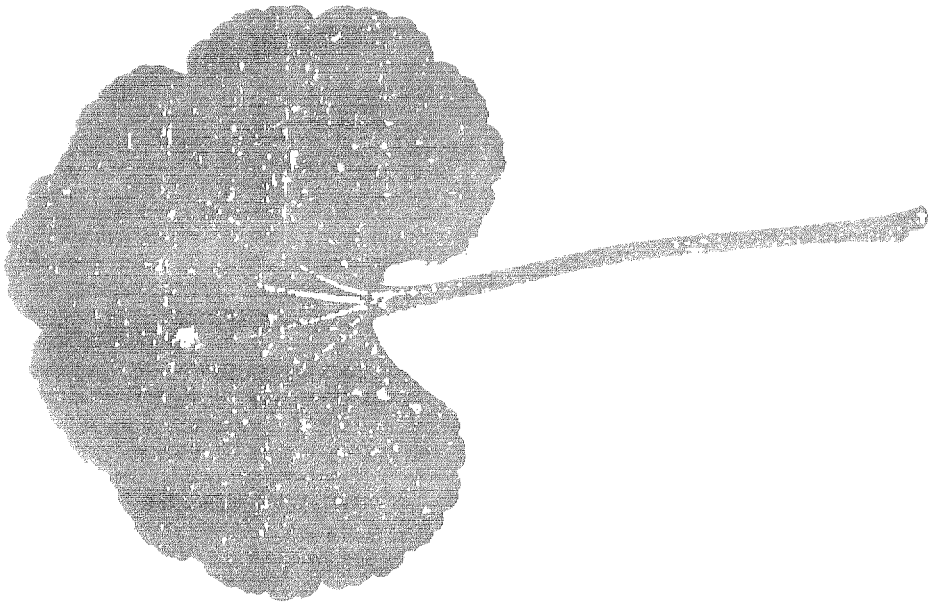
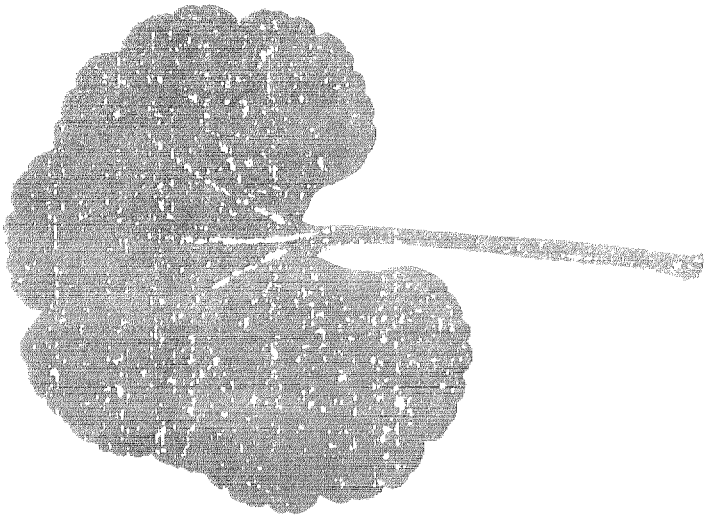

United States Patent [19]

Schumann

[11] Patent Number: Plant 5,369

[45] Date of Patent: Dec. 18, 1984

[54] GERANIUM PLANT NAMED FLIRTPEL

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 547,891

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of geranium named Flirtpel characterized by the combined characteristics of pink flower color, semi-double flower form, cultivation at temperatures below 12° C., relatively small leaves, early spring flowering response, and by its highly floriferous habit.

3 Drawing Figures

The present invention comprises a new and distinct cultivar of geranium, botanically known as *Pelagonium zonale,* and hereinafter referred to by the cultivar name Flirtpel.

Flirtpel is a product of planned breeding program which had the objective of creating new geranium cultivars with good chlorophyll quality for transportation, fast rooting, compact habit with smaller leaves than the cultivar Flirt, and good tolerance for low cultivation temperatures.

Flirtpel was originated from a hybridization made in a controlled breeding program in Hillscheid, Federal Republic of Germany, in 1979 with the hybridization comprising a self-breeding of the cultivar PAC® Purpurball.

Flirtpel was discovered and selected as one flowering plant within the progeny of the stated cross by Ingeborg Schumann on June 27, 1980 in a controlled environment in Hillscheid, Federal Republic of Germany.

The first act of asexual reproduction of Flirtpel was accomplished when vegetative cuttings were taken from the initial selection in January, 1981 in a controlled environment in Hillscheid, Federal Republic of Germany by a technician working under formulations established and supervised by Ingeborg Schumann. Horticultural examination of selected units initiated in the Spring of 1981 and continuing into 1982 has demonstrated that the combination of characteristics as herein disclosed for Flirtpel are firmly fixed and are retained through successive generations of sexual reproduction.

Flirtpel has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Flirtpel, which in combination distinguish this geranium as a new and distinct cultivar:

1. Pink flower color.
2. Semi-double flower form.
3. Flirtpel can be cultivated at temperatures below 12° C.

4. Relatively small leaves, thereby being economical in spacing requirements.
5. An average of 3.3 branches per plant.
6. No growth treatment necessary.
7. Early spring flowering response.
8. Highly floriferous.

Of the many commercial cultivars known to the present inventor, the most similar in comparison to Flirtpel is Pelfi® Flirt and PAC® Rospen. Reference is made to attached Chart A which compares certain characteristics of Flirtpel to those same characteristics of Flirt and Rospen, both unpatented cultivars. In general comparison to Flirt, Flirtpel has smaller leaves, earlier response, greater flower production, a faster rooting time, and better temperature tolerance. In comparison to Rospen, Flirtpel has a more erect peduncle, a different flower color, faster rooting and better branching, earlier response, and much greater flower production.

The accompanying photographic drawings show typical flower and foliage characteristics of Flirtpel, with colors being as true as possible with illustrations of this type. Sheet 1 is a perspective color photograph of a potted plant. Sheet 2 is a relatively enlarged color photograph showing the foliage, bloom and buds, and sheet 3 is a black and white print showing the underside of the foliage.

In the following description color references are made to The Royal Horticultural Society Colour Chart. In certain instances, parallel or alternate values are based on the Horticultural Color Chart (H.C.C.). The color values were determined between 11:20–11:35 A.M. on Aug. 11, 1983 under 25,000 Klux at Hillscheid, Federal Republic of Germany.

CLASSIFICATION

Botanical: A hybrid of the genus *Pelagonium L'Hert.*
Commercial: Flirtpel.

INFLORESCENCE

Umbel:

*Average diameter.*—104 mm.
*Average dpeth.*—74 mm.
*Peduncle length.*—216 mm.
*Pedicel length.*—28 mm. with anthocyan.

Corolla:

*Average diameter.*—48 mm.

*Form.*—Semi-double, not round.

*Color (general tonality from a distance of three meters).*—R.H.S. 67C, H.C.C. 27/1.

*Color(abaxial).*—R.H.S. 68A, H.C.C. 27/1, white at the base.

*Color (adaxial).*—H.C.C. 27/1-26/1.

Bud:

*Shape.*—Narrow elliptic to elliptic.

*Color (abaxial).*—Same color as corolla.

Reproductive organs:

*Androecium.*—Monodelphous, 6 stamens; plentiful pollen.

*Gyneocium.*—Stigma 5-6 lobed, color red; style, color red.

Spring flowering response period: In Hillscheid Federal Republic of Germany in 1982 65% of plants had at least 1 flower open 13 weeks after planting of unrooted cutting.

Outdoor flower production: Flower count in 1982 in Hillscheid, Federal Republic of Germany was between 62 and 72 flowers per plant for June through October observation period.

Durability: Shatter resistance good.

PLANT

Foliage:

*Form.*—Generally kidney shaped.

*Margin.*—Bicrenate.

*Color (abaxial).*—Medium green.

*Tolerance to botrytis.*—Good.

General appearance and form:

*Internode length.*—34 mm.

*Branching pattern.*—3.3 branches per plant.

*Height.*—280 mm., thin stem.

CHART A

| CULTIVAR | Corolla Color | Branching Habit (Number of Branches) | Rooting Time | Plant Height |
|---|---|---|---|---|
| Pelfi ® Flirt | RHS 67C | 3.2 | Slow | Tall |
| PAC ® Rosen | HCC25 with dark eye | 2.7 | Medium | Medium |
| Flirtpel | HCC, 27/1 RHS 67C with white eye | 3.3 | Very fast | Medium |

| CULTIVAR | Spring Flowering Response | Outdoor Flower Production | Attitude of Stems and Peduncles | Zonation |
|---|---|---|---|---|
| Pelfi ® Flirt | 55% | 40-44 | Erect | Middle |
| PAC ® Rosen | 50% | 39-45 | Semi-erect | Middle |
| Flirtpel | 65% | 62-72 | Erect | No |

I claim:

1. A new and distinct cultivar of geranium named Flirtpel, as described and illustrated, and particularly characterized by the combined characteristics of pink flower color, semi-double flower form, cultivation at temperatures below 12° C., relatively small leaves, early spring flowering response, and by its highly floriferous habit.

* * * * *